(12) United States Patent
Mitidieri et al.

(10) Patent No.: US 9,504,666 B2
(45) Date of Patent: Nov. 29, 2016

(54) CHLOROPROCAINE-BASED PHARMACEUTICAL COMPOSITION FOR REPEATED INTRATHECAL ADMINISTRATION

(71) Applicant: SINTETICA S.A., Mendrisio (CH)

(72) Inventors: Augusto Mitidieri, Lugano (CH);
Elisabetta Donati, Cavallasca (IT);
Nicola Caronzolo, Bissone (CH)

(73) Assignee: SINTETICA S.A., Mendrisio (CH)

( * ) Notice: Subject to any disclaimer, the term of this patent is extended or adjusted under 35 U.S.C. 154(b) by 0 days.

(21) Appl. No.: 14/650,583

(22) PCT Filed: Dec. 11, 2013

(86) PCT No.: PCT/IB2013/060801
§ 371 (c)(1),
(2) Date: Jun. 9, 2015

(87) PCT Pub. No.: WO2014/091420
PCT Pub. Date: Jun. 19, 2014

(65) Prior Publication Data
US 2015/0320716 A1    Nov. 12, 2015

(30) Foreign Application Priority Data
Dec. 12, 2012  (IT) .............. MI2012A2120

(51) Int. Cl.
*A61K 31/245* (2006.01)
*A61K 31/573* (2006.01)
*A61K 31/167* (2006.01)
*A61K 9/00* (2006.01)

(52) U.S. Cl.
CPC ........... *A61K 31/245* (2013.01); *A61K 9/0085* (2013.01); *A61K 31/167* (2013.01); *A61K 31/573* (2013.01)

(58) Field of Classification Search
None
See application file for complete search history.

(56) References Cited

FOREIGN PATENT DOCUMENTS

WO    2004/058329       7/2004
WO    2007/028788   *   3/2007

OTHER PUBLICATIONS

Kopacz, D.J., Regional Anesthesia and Pain Medicine, vol. 30, No. 1, Jan. 1, 2005, pp. 36-42.*
Casati et al., Anesthesia & Analgesia (Hagerstown, MD, United States) (2006), 103(1), pp. 234-238.*

(Continued)

*Primary Examiner* — Karl J Puttlitz
(74) *Attorney, Agent, or Firm* — Silvia Salvadori, P.C.; Silvia Salvadori (57) ABSTRACT

This invention relates to an injectable pharmaceutical composition based on chloroprocaine or salts and/or derivatives thereof for use in central loco-regional anesthesia by intrathecal administration in repeated doses. Unexpectedly, the intrathecal administration in repeated doses of chloroprocaine does not increase the neurotoxicity of this drug in statistically significant manner.

9 Claims, 3 Drawing Sheets

(56) References Cited

OTHER PUBLICATIONS

Casati et al., Anesthesia & Analgesia (Hagerstown, MD, United States) (2007), 104(4), 959-964.*

Kopacz, D.J., "Spinal 2-chloroprocaine: Minimum effective dose", Regional Anesthesia and Pain Medicine, Lippincott Williams & Wilkins, U.S., vol. 30, No. 1, Jan. 1, 2005, pp. 36-42.

APP Pharmaceuticals: "Nesacaine-Nesacaine MPF", FDA—U.S. Food and Drug administration (retrieved on Nov. 11, 2013).

Wang et al., "Chronic neurological deficits and nesacaine-CE. An effect of the anesthetic, 2-chloroprocaine, or the antioxidant, sodium bisulfite?" Anesthesia and Analgesia, 1984, U.S., vol. 63, No. 4, 1984, pp. 445-447.

Pollock, J.E.: "Intrathecal chloroprocaine-not yet "safe" by US FDA parameters", International Anesthesiology Clinics, Little Brown, Boston, US, vol. 50, No. 1, Jan. 1, 2012, pp. 93-100.

Craw.ley et al., "Acetominophen prevents hyperalgesia in central pain cascade", Neuroscience Letters, Limerick, IE, vol. 442, No. 1, Sep. 5, 2008, pp. 50-53.

International Search Report of PCT/IB2013/060801 of Feb. 25, 2014.

\* cited by examiner

CHLOROPROCAINE-BASED PHARMACEUTICAL COMPOSITION FOR REPEATED INTRATHECAL ADMINISTRATION

This application is a U.S. national stage of PCT/IB2013/060801 filed on 11 Dec. 2013, which claims priority to and the benefit of Italian Application No. MI2012A002120 filed on 12 Dec. 2012, the contents of which are incorporated herein by reference in their entireties.

FIELD OF THE INVENTION

The present invention relates to a chloroprocaine-based pharmaceutical composition for repeated intrathecal administration.

The present invention originates in the sector of injectable pharmaceutical preparations suitable for spinal or intrathecal anesthesia.

Specifically, the present invention relates to the use of chloroprocaine-based injectable solutions for intrathecal anesthesia.

STATE OF THE ART

Spinal anesthesia is a central loco-regional anesthesia technique in which an injection solution containing a local anesthetic as active principle is injected into the dura mater, i.e. the outer meningeal membrane which protects the spinal cord. Typically, the injection is made using special thin needles between the spinous processes of two vertebrae.

Once injected, the solution containing the local anesthetic mixes with the cerebrospinal fluid which surrounds the spinal cord and is located between the cord and the dura, blocking the conduction of nerve impulses to the brain and causing the reversible loss of sensitivity, which may or may not be accompanied by motor paralysis. The spinal cord in all cases remains protected by the pia mater, the innermost meningeal membrane.

By mixing with the cerebrospinal fluid the solution containing the local anesthetic determines the anesthesia of the front and rear part of the spinal cord, i.e. the regions from where the motor and sensitive fibers originate. The administration of the anesthetic solution thus determines the absence of sensitivity in territories innervated by the concerned nerve roots and at the same time inhibits muscular activity.

Generally, spinal anesthesia is used for operations on organs of the lower abdomen and the lower limbs. Typical examples of the use of spinal anesthesia are appendicectomy, hemioplasty, Caesarian section, knee arthroscopy, bunion correction etc.

When the anesthetic used for spinal anesthesia is isobaric, i.e. has the same specific weight as the cerebrospinal fluid or liquor, all segments are generally concerned, thus producing a response which is commensurate with the amount of injected drug.

The effect of the spinal anesthesia may last for from one to approximately three hours, according to the type of local anesthetic used.

Local spinal anesthesia techniques may be further divided into epidural injection and intrathecal injection. In the latter case, the solution containing local anesthetic is injected locally into the so-called subarachnoid space.

While the intrathecal technique is more invasive than the epidural technique, because the injection concerns an innermore zone of the spinal cord, it has the advantage of requiring considerably lower doses of local anesthetic, approximately ⅒th. This aspect is generally an advantage because local anesthetics have a given neurotoxicity.

Despite this, the intrathecal administration of local anesthetics may also imply neurotoxicity and is not free from drawbacks. These side effects become even more apparent in the case of repeated doses of local anesthetic.

Furthermore, not all local anesthetics provide an adequate response in case of spinal or intrathecal administration. For example, Hodgson P S, Liu S S, Batra M S et al. (Procaine compared with lidocaine for incidence of transient neurologic symptoms, Reg. Anesth. Pain Med, 2000; 25: 218-22) report a percentage of cases refractory to local anesthesia with procaine equal to 17%.

Other local anesthetics, such as lidocaine, provide more adequate responses for spinal administration. However, its use in spinal cord anesthesia implies given risks for the patient's health in all cases.

For example, it is known from Pollock J E. (Transient neurologic symptoms: etiology, risk factors, and managements, Reg. Anesth. Pain Med. 2002; 27: 581-6) that the use of lidocaine in spinal anesthesiological practice is associated to the onset of transient neurologic syndrome (TNS).

Clinical research has thus addressed the use of alternative local anesthetics, such as bupivacaine. With reference to in vivo rat models, Sakura et al. in Anesth. Analg. 2005; 101:541-7 observed that bupivacaine induces less severe morphological damage and functional worsening than lidocaine, when both anesthetics are administrated intrathecally, in equipotent concentrations.

However, bupivacaine is a local anesthetic with long-lasting action, and for this reason its use in spinal anesthesia is often associated to phenomena of urinary retention. Its use is thus limited to cases in which long-lasting spinal anesthesia is required.

Among short-lasting local anesthetics, the use of chloroprocaine is also known. However, the use of this local anesthetic is limited to intrathecal administration today. Indeed, most chloroprocaine formulations currently available on the market (Chloroprocaine Hydrochloride Injection, USP made by Bedford Laboratories, Boehringer Ingelheim and Nesacain®-MPF made by AstraZeneca) are authorized for epidural but not intrathecal application. Consequently, chloroprocaine is currently used only marginally for intrathecal administration.

The use of a single dose of an aqueous solution of chloroprocaine free of preservatives for intrathecal administration is known from Italian patent no. 1366154 by the Applicant.

The presumed neurotoxicity of chloroprocaine has constituted until today a serious deterrent to intrathecal administration of this drug in repeated doses.

Indeed, according to current anesthesiological practice, the repeated spinal or intrathecal administration of chloroprocaine is not only recommended but should be instead avoided in order to limit the risks related to the neurotoxicity of this drug.

For this reason, current medical practice requires to use a different local anesthetic for doses following the first in the cases in which the spinal or intrathecal administration of chloroprocaine must be repeated.

However, in the field of anesthesiology, the recurrent use of spinal and intrathecal anesthesia for one day surgery has increased the demand for drugs with local anesthetic action suitable for repeated intrathecal administration without significantly increasing neurotoxicity risks.

SUMMARY

The applicant of the present invention unexpectedly discovered that 2-chloroprocaine can be repeatedly administrated spinally/intrathecally without detecting the neurotoxicity attributed to the drug.

According to a first aspect, the present invention relates to 2-chloroprocaine and salts and/or derivatives and/or esters thereof for use in central loco-regional anesthesia by intrathecal administration in repeated doses.

Chloroprocaine, or 2-(diethylaminoethyl) 4-amino-2-chlorobenzoate (CAS 3858-89-7), in form of hydrochloride salt (chloroprocaine HCl) is a narcotic substance. The pharmaceutical profile of chloroprocaine, in particular in form of hydrochloride, is similar to that of lidocaine, with a typically short onset of 5-15 minutes and a typically short-lasting effect equal to 30-60 minutes.

In the scope of the present invention, 'chloroprocaine' means a substance as-is or in salified form as chloroprocaine hydrochloride or chloroprocaine derivatives.

The offset of chloroprocaine is rapid; its plasma half-life is indeed comprised in the range from 45 to 60 seconds, which makes it the anesthetic with most rapid offset of those clinically used known today.

According to other aspects, the invention extends to an injectable aqueous solution of chloroprocaine HCl free of preservatives for central loco-regional anesthesia by intrathecal administration in repeated doses According to another embodiment, the chloroprocaine HCl by intrathecal administration in repeated doses is an injectable aqueous solution having pH from 3 to 4.

In some embodiments, the chloroprocaine administered in repeated doses according to the invention has a concentration from 0.5 to 1.5% by weight.

In the scope of the present invention, 'repeated doses' mean the intrathecal administration of at least one dose of chloroprocaine after an initial dose.

In some embodiments, the repeated doses of chloroprocaine are from 2 to 10, e.g. from 3 to 7 subsequent doses, each of which may be typically administered once a day.

In some embodiments, the treatment with repeated doses of chloroprocaine includes the intrathecal administration every day for seven consecutive days.

'Dose of chloroprocaine' means an amount of chloroprocaine and/or salts or derivatives thereof effective to determine a central loco-regional anesthesia when administered intrathecally.

BRIEF DESCRIPTION OF THE DRAWINGS

The present invention will be described in detail below with reference to the figures, in which.

The present invention will now be described with reference to the following examples which are supplied by way of examples only without limiting the invention in any manner.

DETAILED DESCRIPTION OF THE INVENTION

Some embodiments of the invention include the use of an injectable aqueous solution of chloroprocaine or derivatives/salts thereof, in particular chloroprocaine hydrochloride, wherein the aqueous solution is essentially free of preservatives, antioxidants and the pH of which is from 3 to 4.

In particular, the applicant has discovered that, contrary to expectations, the repeated intrathecal administration of chloroprocaine HCl does not determine detectable neurotoxicity and a significant increase in the typical side effects of repeated spinal and intrathecal administration of the local anesthetic.

This discovery is surprising because the indications contained in scientific literature induced anesthesiologists to administer a different type of local anesthesia if needing to administer a second dose of chloroprocaine close to the first.

The essential absence of neurotoxicity of the repeated intrathecal administration of chloroprocaine HCl in aqueous solution, e.g. with pH 3-4, is further surprising. Indeed, one would expect that the repeated administration in the spinal column of a potentially neurotoxic active principle, such as chloroprocaine in a very acid solution, to show evident signs of cell toxicity. On the contrary, there was no clinical evidence of such toxicity using repeated doses of chloroprocaine in accordance with the embodiments of the invention.

Specifically, the inventors have found that contrary to expectations on the basis of common general knowledge, 12 hours after a first intrathecal administration of chloroprocaine HCl even repeated doses of the drug may be injected, without increasing neurotoxicity in statistically significant manner.

In accordance with some embodiments, the invention relates to the intrathecal administration in a human being over 24 hours of at least one dose of an injectable chloroprocaine-based aqueous solution of the afore-described type, repeated every day for a time period from two to ten days.

In accordance with certain embodiments, the present invention provides an injectable pharmacological composition comprising chloroprocaine or the salts and/or derivatives thereof for central loco-regional anesthesia by intrathecal administration of a daily dose of 5-150 mg of chloroprocaine or of a salt and/or derivatives thereof repeated for a time period from 2 to 10 days, typically from 3 to 7 days. In some of these embodiments, the daily dose may be single or fractioned into two-three doses.

In some embodiments, the chloroprocaine dose which may be administered intrathecally ranges from 10 to 100 mg/day, from 15 to 80 mg/day, from 30 to 60 mg/day, repeated for a time period from 2 to 10 days, typically from 3 to 7 days. In accordance with some embodiments, a low-dose solution of chloroprocaine HCl typically of 5-15 mg/ml is administrated intrathecally in repeated doses, for example 1-3 a day, for 2-10 days or 3-7 days.

The intrathecal administration of repeated doses of chloroprocaine HCl, e.g. one dose over 24 hours for three-seven days has the following advantages:

i) a rapid recovery of the organic functions of the patent after the anesthetic treatment. The favorable pharmacological profile of chloroprocaine, which combines fast onset with fast offset, allows the patient to perambulate a short time period after the treatment and to limit the risks of urinary retention found after repeated use of the common local anesthetics having a longer half-life.

ii) a high comfort for patients even after repeated dose administration, e.g. one injection/day for 7 days.

iii) low systematic toxicity because the half-life of chloroprocaine HCl is lower than one minute. This advantage is consequent to the rapid offset of chloroprocaine by virtue of plasma pseudo cholinesterase.

iv) a reduced incidence of typical side effects of the local anesthetics. In particular, the concomitant administration of medium-long-lasting action local anesthetics with opioids, commonly performed to complete the analgesic action, determines the onset of collateral effects, such as itching and skin rashes. With the repeated intrathecal administration of chloroprocaine HCl, the onset of these side effects found with the use of conventional local anesthetics is considerably limited.

In accordance with an embodiment, the present invention includes the intrathecal administration of repeated doses of an injectable aqueous solution comprising 5.0-15 mg of chloroprocaine HCl, 4-12 mg NaCl per 1 ml of water and HCl in an amount sufficient to give a pH from 3.0 to 4.0 to the solution.

An embodiment includes the repeated intrathecal use of an injectable chloroprocaine-based aqueous solution having osmolarity from 270 to 300 mOsm/kg.

According to a further embodiment, the aqueous solution of chloroprocaine HCl used for repeated intrathecal administration has a relative density at 37° C. of 1.0003 to 1.0020 g/ml.

According to some embodiments, the injectable aqueous solution for repeated intrathecal administration comprises an amount of chloroprocaine HCl from 0.5 to 1.5% by weight, preferably 1% ca.

For example, a lumbar trunk anesthesia for short surgery can be obtained by intrathecal administration of a variable amount of chloroprocaine HCl variable from 30 to 50 mg and the administration of the same amount of drug can be repeated the following day with essentially with no side effects.

In some embodiments, the invention relates to a pharmaceutical composition comprising chloroprocaine or salts and/or derivatives thereof for use in central loco-regional anesthesia by intrathecal administration in repeated doses either separate, sequential or simultaneous with an analgesic drug and/or with adrenaline. Typically the dose may be repeated every 2-10 days, preferably every 3-7 days.

Typically, the administration of chloroprocaine in repeated doses may be required whenever the therapeutic need arises, e.g. in the case of repeated surgery, endoscopy, localized persistent pain treatment and further clinical indications, or as palliative cure.

In accordance with another aspect, the present invention relates to a central loco-regional anesthesia method comprising the intrathecal administration in repeated doses of an injectable chloroprocaine-based pharmaceutical composition according to any one of the described or exemplified embodiments.

In certain embodiments, the method of the invention includes the intrathecal administration of at least 5-150 mg dose/day of chloroprocaine HCl every 1-10 days, 3-7 days.

By way of example, it is possible to infuse by intrathecal administration an injectable aqueous solution with an acid pH from 3 to 4, containing from 5 to 15 mg/ml of chloroprocaine HCl, preferably free of preservatives and/or stabilizers, repeated for 2-10 days or 3-7 days.

In some embodiments, a pharmaceutical composition containing chloroprocaine or salts thereof is either administered or infused in repeated doses by means of a spinal catheter. The infusion of the composition or solution of chloroprocaine or a salt thereof according to conventional anesthesiological techniques known by persons skilled in the art.

EXAMPLES

Example 1

A pre-clinical trial was carried out to assess the neurotoxicity of 2-chloroprocaine by intrathecal administration in repeated doses using a saline solution as control.

Results

Group Treated with Saline Solution (Vehicle)

A first group of six rats was repeatedly treated with 20 µl of an injectable saline solution by intrathecal administration once a day.

No significant changes were observed in the behavior of the rats after seven consecutive days of treatment. The rats treated with repeated doses with the vehicle did not show signs of sleepiness, tendency to bite or scratch, regurgitation or vomiting, altered defecation or abnormal salivation.

The motor functions remained entirely unchanged. Only on the seventh day did two of the six rats show partial unilateral paralysis which only slightly influenced normal posture.

The body weight was not influenced by the administration in repeated doses and showed an increasing physiological trend.

The tail flick latency before injecting the vehicle was in line with historical laboratory data and appropriate to the test system. The basic latency indicates a tendency to reduction over the seven days of the test, although in non-significant manner. No evident signs of inflammation or irritation were found in the caudal reasons subject to stimulation by heating.

Figure 1:
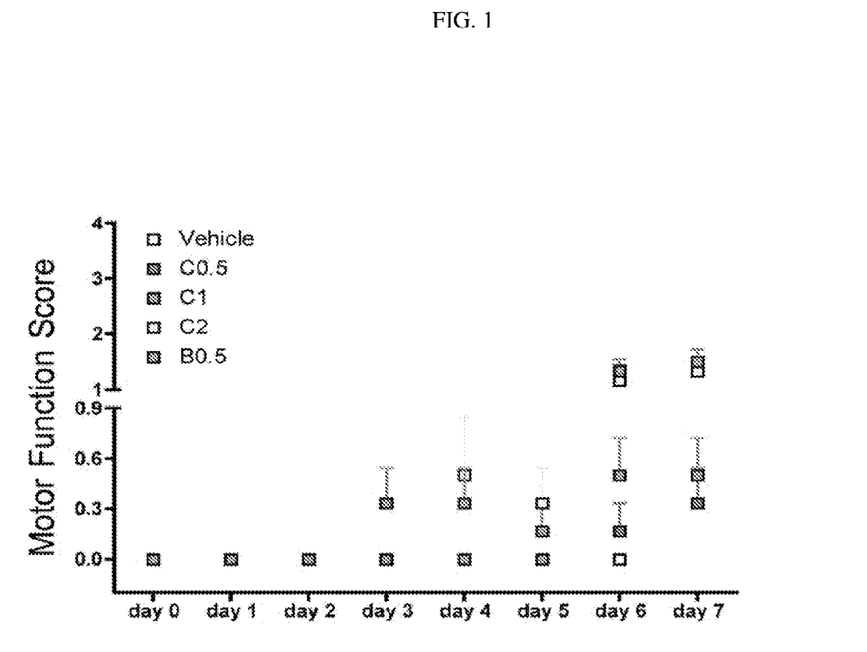
FIG. 1 is a chart showing the motor function score for a group of rats to which a daily dose of vehicle, chloroprocaine 0.5%, chloroprocaine 1%, chloroprocaine 2% and bupivacaine 0.5% was administered for seven consecutive days intrathecally according to the protocol illustrated in Example 1 below.
Figure 2:
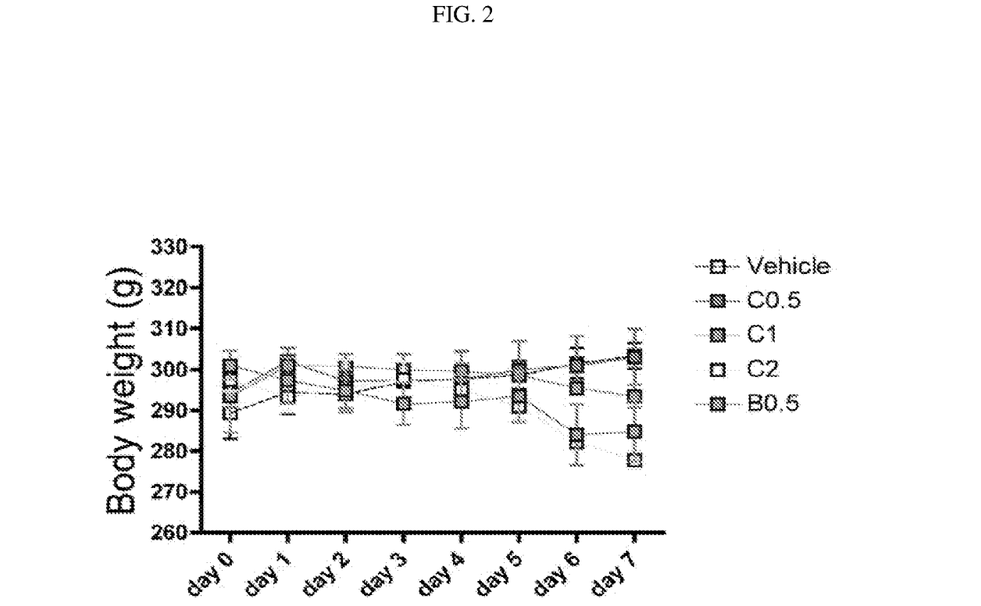
FIG. 2 is a chart showing the weight variation of the rats treated for seven consecutive days by intrathecal administration with repeated daily dose of vehicle, chloroprocaine 0.5%, chloroprocaine 1%, chloroprocaine 2% and bupivacaine 0.5% according to the test in Example 1. The data are presented as ±SEM average of 6 rats.
Figure 3:
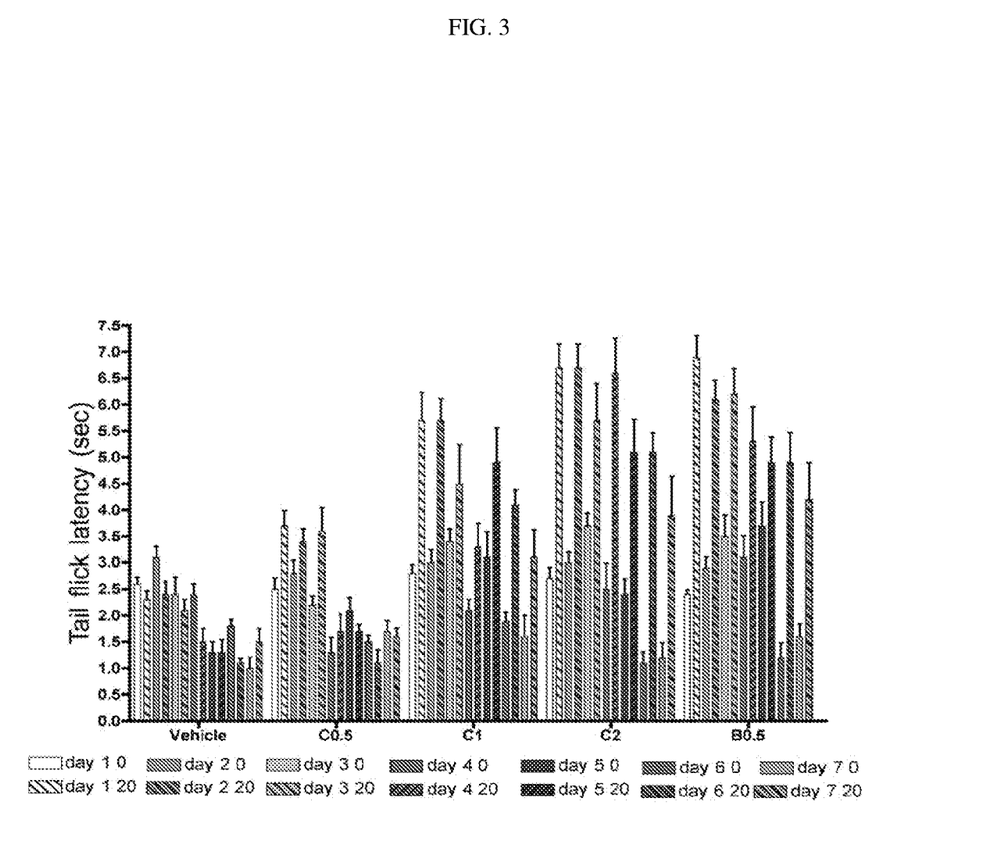
FIG. 3 is a chart showing the tail flick latency of rats treated for 7 consecutive days by intrathecal administration with daily dose of vehicle, chloroprocaine 0.5%, chloroprocaine 1%, chloroprocaine 2% and bupivacaine 0.5% according to the test in Example 1. The data are presented as ±SEM average of 6 rats.
Figure 4:
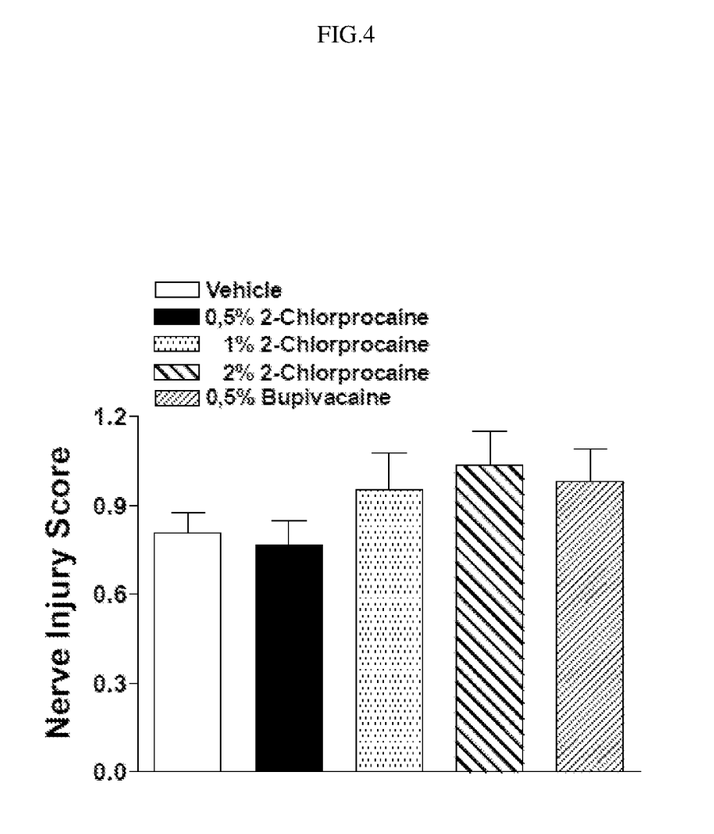
FIG. 4 is a chart showing the nerve injury score in sections obtained from a 10 mm caudal portion of *conus medullaris* (*cauda equina*) in rats treated for 7 days by intrathecal administration with repeated doses of vehicle, chloroprocaine 0.5%, chloroprocaine 1%, chloroprocaine 2% and bupivacaine 0.5% according to the test in Example 1. An injury score from 0 to 3 was attributed to each section. The injury score for each cross section was calculated as average score of all clusters in each section. The data are presented as ±SEM average of 6 rats.

A 10 mm portion of the *conus medullaris* (*cauda equina*) was analyzed seven days after the intrathecal injection. The histological score was 0.809±0.067. The results are summarized in the chart shown in FIG. 4.

2-Chloroprocaine 0.5% Group (C0.5)

No appreciable changes in behavior were observed after injecting 20 µl of 2-chloroprocaine 0.5% until the seventh day of the trial. The rats treated repeated by intrathecal administration of a dose of 2-chloroprocaine 0.5% a day did not show signs of sleepiness, tendency to bite or scratch, regurgitation or vomiting, altered defecation or abnormal salivation. Motor functions remained unchanged. Signs of partial unilateral paralysis (score 1), which only partially influenced normal posture, appeared on the sixth day in one rat and on the seventh day in two rats.

Body weight was not altered by the administration of 20 µl of 2-chloroprocaine 0.5% and showed a physiologically increasing trend.

No statistically significant difference was observed by comparing the administration of 20 µl of 2-chloroprocaine 0.5% with the group treated with the vehicle (F=0.12 DFn=1, DFd=70 Pvalue=0.7337).

The tail flick latency before injecting 20 µl of 2-chloroprocaine 0.5% was comparable with the values of rats treated with vehicle. The basic latency indicated a reduction tendency over the seven days of the test although in non-significant manner. No evident signs of inflammation or irritation were found in the caudal regions subject to stimulation by heating.

The administration of 20 µl of 2-chloroprocaine 0.5% caused a slight increase of tail flick latency after 20 minutes of exposure, although this effect was not significant from the statistic point of view.

The histological score did not show statistic differences when 2-chloroprocaine 0.5% compared with the control group (0.764±0.083).

2-Chloroprocaine 1% Group (C1)

No appreciable changes in behavior were observed after injecting 20 µl of 2-chloroprocaine 1% until the seventh day of the trial. The rats were treated repeatedly by intrathecal administration of a dose of 2-chloroprocaine 1% a day did not show signs of sleepiness, tendency to bite or scratch, regurgitation or vomiting, altered defecation or abnormal salivation.

Motor functions: signs of partial unilateral paralysis (score 1), which only partially influenced normal posture, appeared on the fifth day in one rat and on the sixth and seventh day in two rats.

Body weight was not altered by the administration of 20 µl of 2-chloroprocaine 1%.

No statistically significant difference was observed by comparing the administration of 20 µl of 2-chloroprocaine 1% with the group treated with the vehicle (F=0.05 P value=0.8353).

Tail flick latency before injecting 20 µl of 2-chloroprocaine 1% was comparable with the values of rats treated with vehicle.

A significant increase of tail flick latency was observed 20 minutes after injecting 20 µl of 2-chloroprocaine 1% and this effect was statistically significant in the trial (P<0.05).

The histological score did not show statistic differences when 2-chloroprocaine 1% was compared with the control group (0.954±0.122). A moderately inflammatory infiltrate in some fibers was identified in two rats.

2-Chloroprocaine 2% Group (C2)

No appreciable changes in behavior were observed after injecting 20 µl of 2-chloroprocaine 2% until the seventh day of the trial, including a single rat with diarrhea on the sixth and seventh day.

The rats treated repeatedly by intrathecal administration of a dose of 2-chloroprocaine 2% a day did not show signs of sleepiness, tendency to bite or scratch, regurgitation (except for one) or vomiting, altered defecation or abnormal salivation.

Motor functions: two rats showed partial unilateral paralysis (score 1) on the third day which only partially influenced normal posture. The symptoms became bilateral for one rat on the fourth day. A change of posture (score 1) was observed in all rats on the sixth day, while two rats showed bilateral weakness which influenced perambulation on the seventh day (score 2).

The body weight decreased after administering 20 µl of 2-chloroprocaine 2%, showing a clear reduction trend along the study period. The effect did not reach statistic significance when compared with the group treated with vehicle in an experiment of these proportions (F=1.37 value P=0.2691).

Tail flick latency before injecting 20 µl of 2-chloroprocaine 2% was comparable with the values of rats treated with vehicle.

A significant increase of tail flick latency was observed 20 minutes after the administration by injecting 20 µl of 2-chloroprocaine 2% and this effect was statistically significant in the trial (P<0.001).

The histological score showed no statistic differences when 2-chloroprocaine 2% was compared with the control group (1.034±0.1170). A moderately inflammatory infiltrate in some fibers was identified in three rats.

Bupivacaine 0.5% Group (B0.5)

Changes of behavior were observed after injecting 20 µl of bupivacaine 0.5% to the seventh day of the study included modest sleepiness in one rat on the fifth day and in two rats on the sixth and seventh days. Excluding these rats, the other animals of the group repeated by intrathecal administration of a dose of bupivacaine 0.5% a day did not show signs of sleepiness, tendency to bite or scratch, regurgitation (except for one) or vomiting, altered defecation or abnormal salivation.

Motor functions: two rats showed partial unilateral paralysis (score 1) on the third and fourth day which only partially influenced normal posture. A change of posture (score 1) could be observed in all rats on the sixth day. Furthermore, two rats on the sixth day and three rats on the seventh day showed bilateral limbic weakness which influenced perambulation (score 2).

Body weight decreased by 0.5% during the administration of bupivacaine, showing a clear reduction trend during the study period compared with that shown for group C2. The effect did not reach statistic significance when compared with the group treated with vehicle in an experiment of these proportions (F=0.54 P value=0.4785).

Tail flick latency before injecting 20 µl of bupivacaine 0.5% was comparable with the values of rats treated with vehicle.

A significant increase of tail flick latency was observed 20 minutes after the administration by injecting 20 µl of bupivacaine 0.5% and this effect was statistically significant in the trial (P<0.001).

The histological score did not show statistic differences by comparing bupivacaine 0.5% (0.979±0.110) with the control group. A moderately inflammatory infiltrate in some fibers was identified in one rat.

Conclusions

The test frequency and the repeated injection tended to make some rats irritable, but this aspect appeared to be independent from the drug because it was also observed in animals treated with the vehicle.

The increased variability of the measurements observed during the study is likely referred to this.

Furthermore, rats have a high learning capacity and this explains the basic tail flick latency observed over the 7 day period.

This trial, including the post-surgery recovery period, uses the maximum period of time for which rats could be maintained easily and safely with spinal catheter.

Only minor alterations in behavior was observed in all trial groups. With regards to the worsening of motor functions, it is apparent that the repeated administration of effective doses of local anesthetics produces an increased incidence of alterations, evaluated as abnormal posture and in some cases as limbic weakness.

On the other hand, concentrations of 2-chloroprocaine 2% and bupivacaine 0.5% appeared less tolerated than other administered concentrations in nearly equivalent manner; it is not instead possible to establish substantial differences between the treated groups of animals in terms of neurological damage after carrying out behavior and motor functionality tests.

The histo-pathological assess of a 10 mm caudal portion of the *conus medullaris* (*cauda equina*) confirmed the behavioral observations. No obvious alterations were observed in the treatment groups. In some cases, it was possible to identify a moderately inflammatory infiltrate in some fibers after repeated administrations of 2-chloroprocaine 1 and 2% and of bupivacaine 0.5%.

Example 2

Standard Protocol

The repeated anesthesia protocol included the slow injection by intrathecal administration of an injectable solution containing chloroprocaine HCl 0.5%, 1.2% NaCl, and HCl in amount sufficient to give a pH of 4.

The chloroprocaine solution was injected once a day for three consecutive days.

Example 3

Standard Protocol

The repeated anesthesia protocol included the slow injection by intrathecal administration of an injectable solution containing chloroprocaine HCl 1.5%, 0.4% NaCl, and HCl in amount sufficient to give a pH of 3.

The chloroprocaine solution was injected once a day for 7 consecutive days.

Example 4

Standard Protocol

The repeated anesthesia protocol included the slow injection by intrathecal administration of an injectable solution containing chloroprocaine HCl 1.0%, 0.72% NaCl, and HCl in amount sufficient to give a pH of 3.5, to which dexamethasone phosphate 0.4% as corticosteroids anti-inflammatory was added.

The combined chloroprocaine/dexamethasone solution was injected once a day for 3 consecutive days.

Example 5

Standard Protocol

The repeated anesthesia protocol included the slow injection by intrathecal administration of an injectable solution containing chloroprocaine HCl 1.0%, 0.72% NaCl, and HCl in amount sufficient to give a pH of 3.5, to which a 2% solution of acetaminophen was added.

The combined chloroprocaine/acetaminophen solution was injected once a day for 7 consecutive days.

Example 6

Anesthetic pharmaceutical composition for intrathecal use having the following mg/ml formula:

| Chloroprocaine HCl | 5 mg |
|---|---|
| NaCl | 7 mg |
| Water | 1 ml |
| HCl | to adjust pH from 3 to 4. |

Example 7

Anesthetic pharmaceutical composition for intrathecal use having the following mg/ml formula:

| Chloroprocaine HCl | 15 mg |
|---|---|
| NaCl | 4 mg |
| Water | 5 ml |
| HCl | enough to adjust pH from 3 to 4. |

Example 8

Anesthetic pharmaceutical composition for intrathecal use having the following mg/ml formula:

| Chloroprocaine HCl | 75 mg |
|---|---|
| NaCl | 2.3 mg |
| Water | 5 ml |
| HCl | to adjust pH from 3 to 4. |

The invention claimed is:

1. A method of central loco-anesthesia comprising the intrathecal administration of an injectable pharmaceutical aqueous solution of chloroprocaine or salts thereof, which is preservatives and/or antioxidant free and has a pH from 3 to 4, wherein the dosage of chloroprocaine administered is from 15 to 80 mg/day daily and wherein said intrathecal administration is repeated for a time period of 2 to 10 days.

2. The method according to claim 1, wherein the dosage of chloroprocaine administered is from 30 to 60 mg/day.

3. The method according to claim 1, comprising the intrathecal administration of the injectable pharmaceutical aqueous solution of chloroprocaine or salts thereof in combination with adrenaline and or an analgesic drug.

4. The method according to claim 1, wherein the chloroprocaine salts is chloroprocaine HCl.

5. The method according to claim 1, wherein the intrathecal administration comprises the administration of said a daily dose repeated for a period of 3 to 7 days.

6. The method according to claim 1, wherein the injectable pharmaceutical aqueous solution of chloroprocaine comprises chloroprocaine HCl, sodium chloride, sterile water and hydrochloride acid.

7. The method according to claim 1, wherein the injectable pharmaceutical aqueous solution of chloroprocaine comprises an amount of chloroprocaine from 0.5 to 1.5% by weight.

8. The method according to claim 1, wherein the injectable pharmaceutical aqueous solution of chloroprocaine comprises 5-15 mg of chloroprocaine HCl/ml of water, 4-12 mg of NaCl and HCl in an amount sufficient to reach a pH of 3.0-4.0.

9. The method according to claim 3, wherein the analgesic drug is selected from acetaminophen, NSAIDs, corticosteroids and opiate drugs.

* * * * *